United States Patent [19]

Zmora

[11] Patent Number: 5,708,691
[45] Date of Patent: Jan. 13, 1998

[54] X-RAY COMPUTED TOMOGRAPHIC IMAGING DEVICE AND X-RAY COMPUTED TOMOGRAPHIC METHOD

[75] Inventor: Ilan Zmora, Skokie, Ill.

[73] Assignee: Kabushiki Kaisha Toshiba, Kawasaki, Japan

[21] Appl. No.: 675,833

[22] Filed: Jul. 5, 1996

[51] Int. Cl.⁶ .................................................. A61B 6/03
[52] U.S. Cl. ............................................ 378/4; 378/901
[58] Field of Search ................................ 378/4, 19, 901

[56] References Cited

U.S. PATENT DOCUMENTS

| | | | |
|---|---|---|---|
| 4,965,726 | 10/1990 | Heuscher et al. | 364/413.19 |
| 5,377,250 | 12/1994 | Hu et al. | 378/15 |
| 5,430,783 | 7/1995 | Hu et al. | 378/15 |
| 5,481,583 | 1/1996 | Heuscher | 378/4 |
| 5,541,971 | 7/1996 | Saito | 378/15 |
| 5,577,501 | 11/1996 | Flohr et al. | 128/653.1 |

FOREIGN PATENT DOCUMENTS

| | | |
|---|---|---|
| 4-224736 | 8/1992 | Japan. |
| 7-194590 | 8/1995 | Japan. |

OTHER PUBLICATIONS

Journal of the Japanese Institute of Electronic information Communication, DII vol. J 74-D-II, No. 8, pp. 1108-1114, Aug. 1991, Hiroyuki Kudo, et al., "Three-Dimensional Helical-Scan Computed Tomography Using Cone-Beam Projections".

*Primary Examiner*—David P. Porta
*Assistant Examiner*—David Vernon Bruce
*Attorney, Agent, or Firm*—Oblon, Spivak, McClelland, Maier & Neustadt, P.C.

[57] ABSTRACT

A computed tomography method and system where a voxel of a subject irradiated with x-rays is divided into an plurality of sub-voxels, and backprojection data is obtained for the sub-voxels. Projection data for the sub-voxels can be weighted before backprojecting, or the projection data can be backprojected and then weighted. With the method according to the invention, instead of backprojecting data on a straight line passing through the center of a voxel, the beam passing through the entire voxel is backprojected. Also, the method and system weights the sub-voxels using a space-variant function. The weighting can be applied to discrete sub-voxels or integration can be used with infinitely thin sub-voxels. The present invention is a more accurate method and can take into account of spreading of the x-ray beam.

20 Claims, 12 Drawing Sheets

(10 ROWS)

(1000 ELEMENTS)

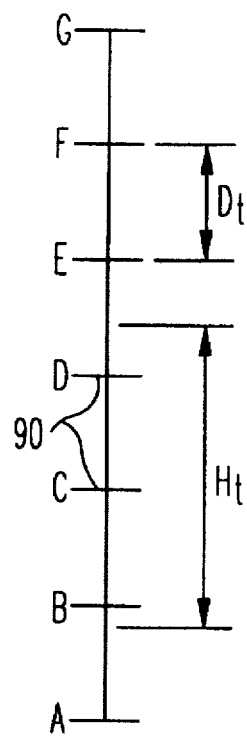
*FIG. 11*
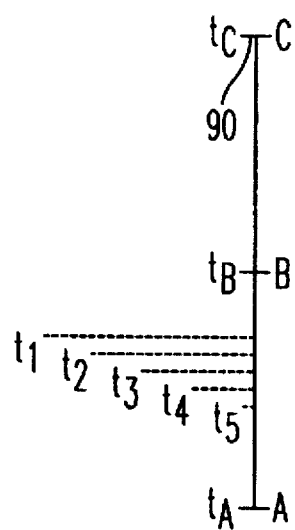
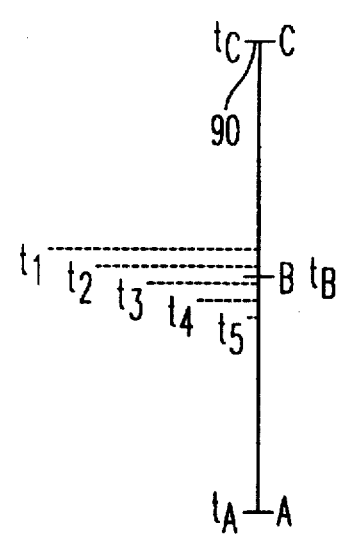
*FIG. 12A*  *FIG. 12B*

X-RAY COMPUTED TOMOGRAPHIC IMAGING DEVICE AND X-RAY COMPUTED TOMOGRAPHIC METHOD

BACKGROUND OF THE INVENTION

1. Field of the Invention

The present invention relates to an x-ray computed tomographic imaging device and an x-ray computed tomographic method, and more particularly to a device and method where voxels of a subject scanned by an x-ray beam is divided into a number of sub-voxels and backprojection is performed using the sub-voxels.

2. Discussion of the Background

Third-generation CT is defined as a system in which, as shown in FIG. 16, an x-ray tube 160 that generates an x-ray flux 161 and an x-ray detector 162 having detector elements 163 (for example, 1000) arranged facing the tube on the opposite side of the subject are rotated about the subject while projection data is collected from various angles. The x-ray flux 161 completely covers the field of view (FOV) or slice of the subject 164. Conventionally, the x-ray flux 161 consisted of a fan-shaped beam of x-rays, and the detector 162 was a one-dimensional array-type x-ray detector.

Two types of scanning systems are employed: conventional scanning and helical scanning. As shown in FIG. 17(a), conventional scanning is defined as a scanning system in which the x-ray tube 160 is moved around the periphery of the same circular track indicated by arrow 170. As shown in FIG. 17(b), a helical scanning system is defined as a scanning system wherein the x-ray source 160 and the detector 162 rotate continuously about the subject and the bed on which the subject is placed is moved along the body axis synchronously with this revolution; this term is employed because, considering a moving co-ordinate system that moves with the subject, the x-ray tube describes a helical orbit 171. In the moving co-ordinate system, the distance in the body-axis (or z-axis) direction through which the x-ray tube is displaced in one rotation is defined as the helical pitch, indicated as 172.

In recent years CTs, known as third generation or fourth generation CTs, have an x-ray tube that generates a cone-beam of x-ray flux that widens out in the direction of the body axis, rather than a fan-shaped beam of x-ray flux, and a two-dimensional array-type x-ray detector wherein the detector elements are arranged in matrix fashion. The x-ray detector has a plurality of one-dimensional array-type detectors are stacked in a plurality of rows, for example N rows, in the z-axis direction. This is called cone-beam CT.

At this point, consider an x-ray beam incident on detectors constituting a single row as shown in FIGS. 18 and 19. X-rays from focal spot 180 are emitted in a cone beam 182 through a collimator 185 onto detector array 183 having detector rows D1-DN. The thickness in the direction of the z-axis when this x-ray beam passes through the center of revolution 181 (center of the z-axis i.e. imaging region field of view) is defined as the basic slice thickness 184 of a cone-beam CT. Also, the imaging region in a third generation cone-beam CT is defined as a cylinder of radius omega centered on the z-axis. Several image reconstruction methods in the case of scanning with a conventional cone-beam CT are known.

In "Practical Cone-Beam Algorithm" by Foldkemp et al, J. Opt. Soc. Am. A, vol. 1, no. 6, pp. 612–619 (June 1984), a method of reconstruction is described, termed the Foldkemp reconstruction method from the name of its developer.

It is an approximate three-dimensional reconstruction algorithm obtained by expanding the fan beam (in a two-dimensional plane) reconstruction algorithm (which is a mathematically straight reconstruction method) in the z-axis direction. It comprises the following steps:

(1) Correction and weighting of projection data: The beam-spreading effect is corrected by multiplying the projection data by weights corresponding to the z-coordinate.

(2) Convolution: The data of (1) are convolved with a reconstruction function which is the same as in fan-beam reconstruction.

(3) backprojection: The data of (2) are added at points (voxels) on the path that the x-rays pass through (from the focal point to the detector).

Image reconstruction is achieved by repeating the above steps (1) to (3) over prescribed angles (360° or 180°+fan angle). In all of the above, the results of computer simulation are given after the mathematical processing. This method of reconstruction is basically an approximate method, so the image quality of the reconstructed image deteriorates as the spread of the beam in the z-axis direction increases, i.e. as the cone angle increases. This imposes limitations on the cone angle that is practicable in medical equipment, etc. Also, various methods of reconstruction involving partial modification of the above by, for example, altering the direction of the convolution processing have been reported, and, regarding Feldkamp reconstruction, many experiments have been reported involving the use of computer simulation and/or imaging plates etc.

One limited version of a multi-slice computed tomography system already exists commercially. However, commonly existing single slice CT systems employ an array of x-ray detectors which extend in a line or in an arc in the transverse plane (the transverse plane is also called the scan plane or the x-y plane). The x-ray source is collimated in such a way as to limit the x-ray radiation only to the detector array. As a result of this geometry, in the static scan mode the data collected by the detector array during one revolution of the x-ray source and the x-ray detectors pertains to one plane which is defined by the x-ray focal spot and the array of detectors, and the ensuing image shows a cut through the scanned object at this same plane. In the helical scan, the object moves in the axial direction during the scan, so that the data collected during the scan corresponds to longer axial length. However the data is still collected along the same plane in space, although the object is now in motion relative, to this plane. In order to speed up the process of data collection, x-ray CT cone beam multi-slice systems will use a multi-slice arrangement of detectors. This multi-slice arrangement of detectors can be obtained by actually stacking several layers of detector arrays in the axial direction, or by using other area detectors such as x-ray image intensifier and more. The x-ray source is now collimated as to allow the x-ray radiation to he collected by all the area of detector arrays thus covering a larger volume than in the case of single slice systems. Multi-slice scanners can be used in the static mode, covering a larger volume in one scan, but their largest advantage will be achieved in helical scans where the gain in the speed along the axial direction will be proportional to the number of slices. The "cone beam" part in the name of the described systems refers to the fact that radiation of the x-ray source ex%ends a cone-like portion of space, or in other words, the radiation diverges from one spot. Consequently, the planes defined by the different detector arrays and the focal spot (detection planes), are not parallel to each other, but also converge towards the x-ray focal spot.

The last fact, the convergence of the detection planes, is currently a weakness of x-ray CT cone beam multi-slice systems, because images reconstructed with the commonly available reconstruction algorithms sometimes result in artifacts in the images.

Two commonly available reconstruction methods are the multi-slice cone beam reconstruction and the Foldkemp reconstruction. These two methods of reconstruction differ by the way in which the z-direction dependence of the raw data and the images, is treated in the reconstruction. Both reconstruction methods can he used in both static scans and, with certain modifications, in helical scans. With the same geometry, images generated with the Foldkemp reconstruction are superior compared to those generated with the multi-slice cone beam reconstruction but at larger cone angles they also suffer from the same artifacts.

SUMMARY OF THE INVENTION

An object of the present invention is provide a system and method to generate finite reconstruction width images.

Another object of the invention is to reduce or eliminate cone beam related artifacts.

A further object of the invention is to reduce or eliminate artifacts caused by the helical motion.

A still further object of the invention is to provide a system and method with improved image quality by improving the S/N (signal to noise) ratio.

These and other objects of the invention are obtained by a computed tomography system and method of operating the system where voxels of a subject scanned by the system are divided into sub-voxels, and backprojection is performed using the sub-voxels.

The system can contain an x-ray source, an x-ray detector, and circuits to obtain and process projection and backprojection data. The system can also contain circuitry for interpolation of projection data, and weighting of the projection data and backprojection data.

The backprojection could be performed for each sub-voxel and then summed or weighted and averaged to produce the backprojection for the voxel containing the sub-voxels. Alternatively, the projection data for the sub-voxels can be weighted and then the weighted data can be backprojected, thus requiring only a single backprojection for all of the sub-voxels.

The data can also be weighted using a space-variant function. The sub-voxels can be weighted in discrete slices, a discrete weighting process, or the number of sub-voxels in a voxel can be allowed to approach infinity, a continuous weighting process. In the discrete process the weighting can be linear or non-linear, and can depend upon the number of detector elements that contribute to the sub-voxel back-projection. In the continuous process, integration is used and the weighting can also depend upon the number of detector elements that contribute to the backprojection.

BRIEF DESCRIPTION OF THE DRAWINGS

Many of the attendant advantages of the invention are apparent from the following detailed description taken in conjunction with the following drawings, wherein:

FIG. 11 is a diagram used in explaining continuous sub-voxel weighting for Foldkemp reconstruction;

FIGS. 12(a) and 12(b) are diagrams illustrating a relationship between a voxel and detector elements used in reconstruction;

DETAILED DESCRIPTION OF THE PREFERRED EMBODIMENTS

Figure 1:
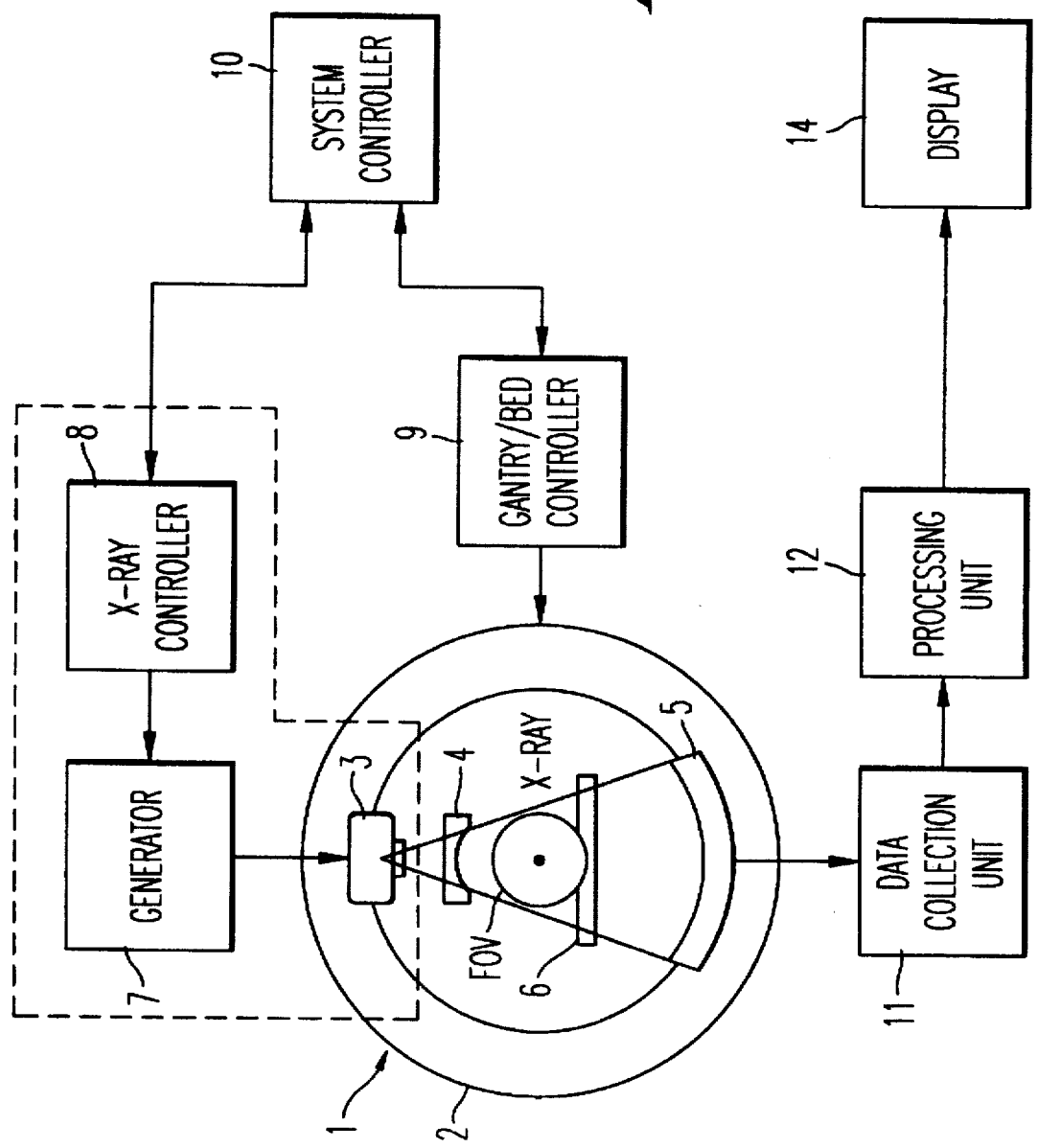
FIG. 1 is diagram of an x-ray computed tomographic imaging device according to a first embodiment of the invention.
Figure 2:
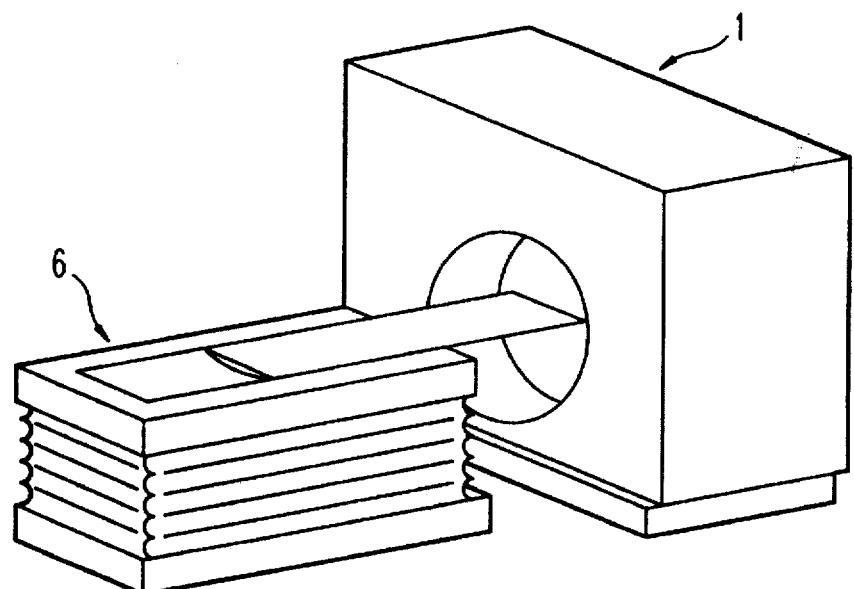
FIG. 2 is a perspective view of a gentry of FIG. 1.
Figure 3:
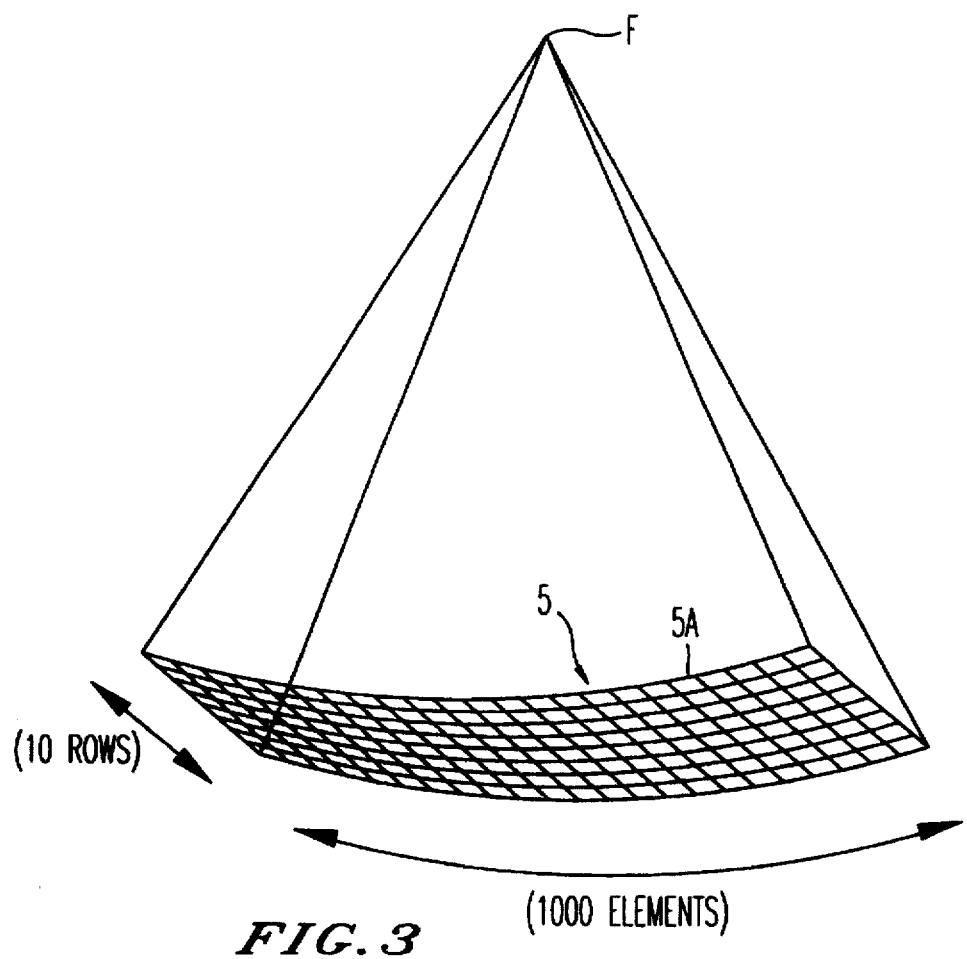
FIG. 3 is a perspective view of a two-dimensional array type x-ray detector of FIG. 1.

The preferred embodiments of the present invention will be described below with reference to the drawings, in particular FIG. 1 which shows an x-ray computed topographic imaging device according to a first embodiment of this invention. FIG. 2 is a perspective view of the gentry of FIG. 1 and FIG. 3 is a perspective view of a two-dimensional array type detector of FIG. 1. The projection data measurement system constituted by gentry 1 accommodates an x-ray source 3 that generates a cone-beam of x-ray flux approximately cone-shaped, and a two-dimensional array type x-ray detector 5 consisting of a plurality of detector elements 5A arranged in two-dimensional fashion, i.e., a plurality of elements arranged in one dimension stacked in a plurality of rows. In FIG. 3, ten rows each having 1000 elements are shown (other arrangements are possible), with the x-ray flux shown schematically emitted from focal point F.

X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to reconstruction processing unit 12. Reconstruction processing unit 12 uses the projection data to find backprojection data reflecting the x-ray absorption in each voxel. In the helical scanning system using a conebeam of x-rays as in the first embodiment, the imaging region (effective field of view) is of cylindrical shape of radius ω centered on the axis of revolution. Reconstruction processing unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Figure 4A:
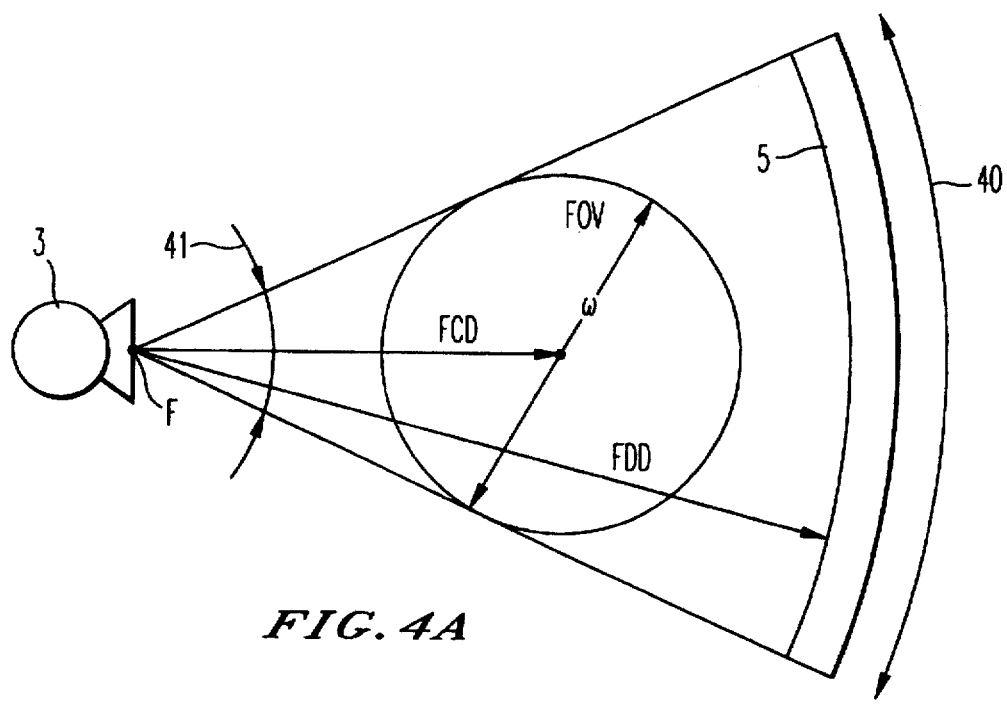
FIGS. 4(a) and 4(b) are diagrams illustrating various parameters of the device.
Figure 4B:
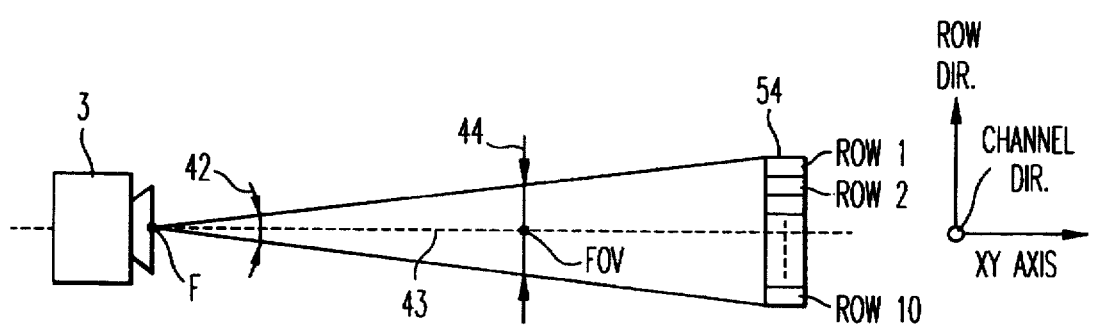
Figure 17B:
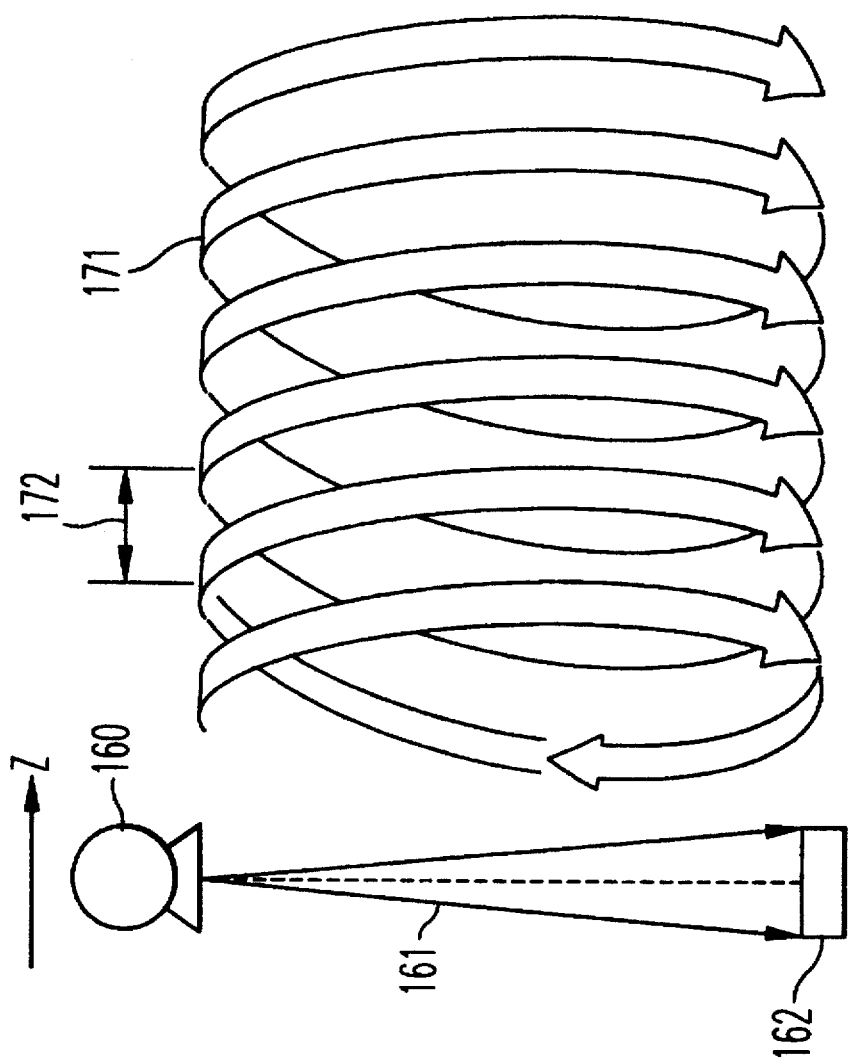
FIGS. 17(a) and 17(b) are diagram illustrating conventional scanning and helical scanning.
Figure 17A:
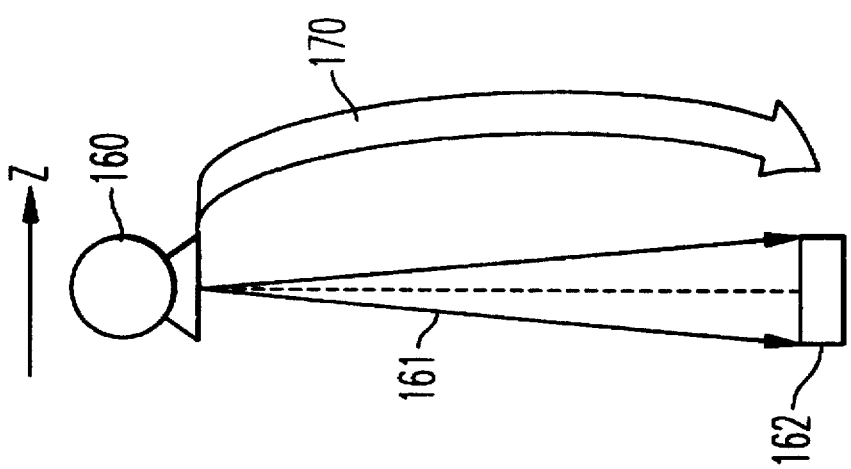
Figure 18:
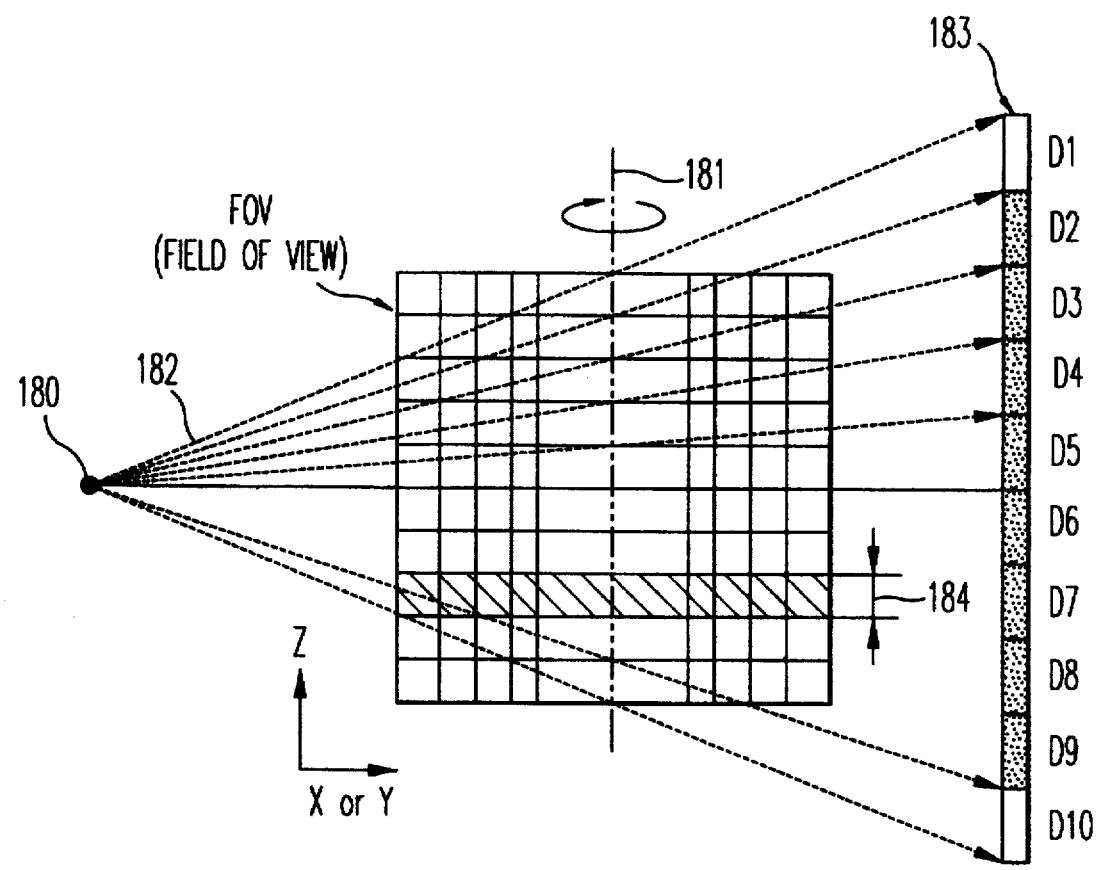
FIG. 18 is a diagram illustrating slice thickness.

Next, the operation of this system will be described. For the system geometry, as one example, N=10, Thick=2 mm, FCD=500 mm, and FOV=240 mm will be selected. As shown in FIG. 4(a) and FIG. 4(b), N is the number of detector rows, Thick is the thickness of the basic slice, FCD is the focal point—center of revolution distance, ω is the diameter of the imaging region FOV (effective field of view), and P is the helical pitch. Also shown in FIG. 4(a) is the fan angle 41, the channel direction 40 and the focal point to detector array distance FDD. The basic slice thickness is defined as the thickness of the x-ray beam incident on a detector element 5A corresponding to one channel in the vicinity of the imaging region FOV. The helical pitch P is defined as the separation of the helical track of x-ray source 3 (see reference numeral 172 in FIG. 17(b)); specifically, it is defined as the distance moved by the sliding sheet while x-ray source 3 performs one revolution.

In FIG. 4(b), x-ray source 3 emits a beam of x-rays having a cone angle 42 and a central plane 43. The total basic slice thickness is illustrated as 44. The x-ray beam passes through the imaging region FOV and is incident upon rows 1–10 of the detector elements 5A.

Figure 5A:
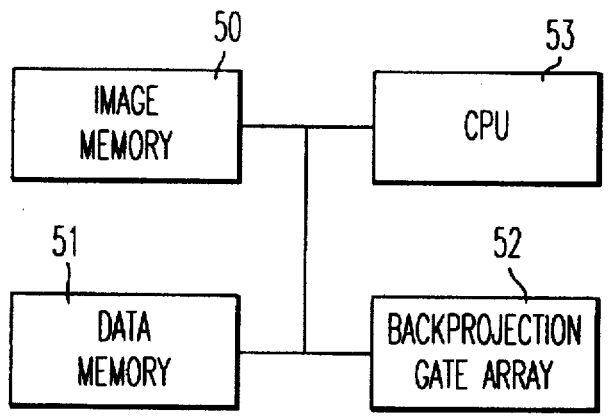
FIGS. 5(a) and 5(b) are diagrams of the reconstruction processor according to the invention.

A detailed explanation of the first embodiment of the invention will now be given. FIG. 5(a) shows the reconstruction processor according to the first embodiment. Projection data from circuit 11 are stored in data memory 51. An image memory 50 is provided for storage of reconstructed image data or storage of data which are being reconstructed. Memories 50 and 51 can be implemented as RAM or other semiconductor memory. Backprojection gate array 52 consists of a weighting circuit, an interpolation circuit and a backprojection circuit, and carries out weighting, interpolation and backprojection operations. Circuits 50–52 and their operations are controlled by CPU 53. CPU 53 can determine an overlap area of x-ray beams, perform the operations of the weighting circuit included in the gate array 52, and carry out desired processing on the projection data such as convolution. A separate convolution circuit may be provided in the circuit of FIG. 5(a). In the following description projection data refers to data both before and after processing such as convolution.

Figure 5B:
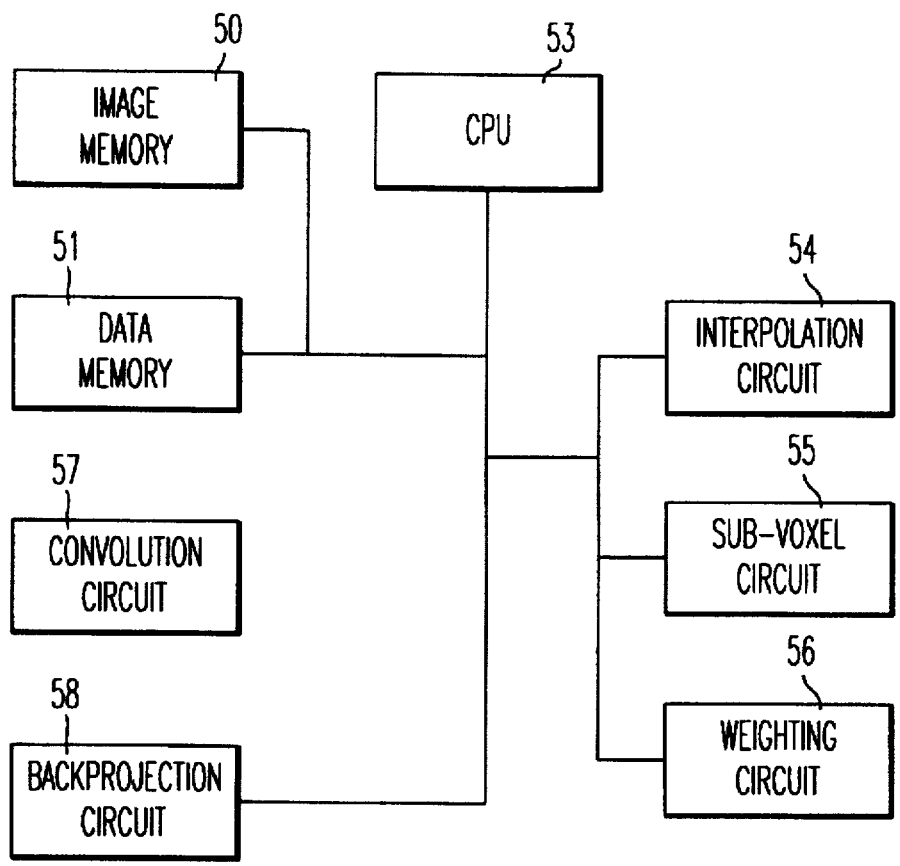

A more detailed diagram of another construction of the reconstruction processor 12 is shown in FIG. 5(b). Image memory 50 and data memory 51 are connected to CPU 53. Also connected to, and controlled by CPU 53 is a convolution circuit 57 that performs convolution or other required processing on the projection data and backprojection circuit 58 performs backprojecting. The processor 12 also includes an interpolation circuit 54, a sub-voxel circuit 55 and a weighting circuit 56. The circuits 54–56 carry out the interpolation, sub-voxel processing and weighting functions described in detail below. The processors 12 shown in FIGS. 5(a) and 5(b) could be implemented in hardware, such as a programmed microcomputer, or could be implemented as software. For example gate array 52 could be implemented as a semiconductor gate array.

Figure 6:
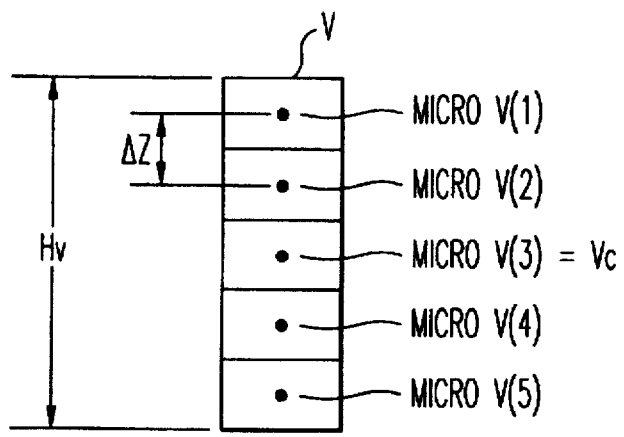
FIG. 6 is a diagram illustrating points arranged with equal interval $\Delta Z$ vertically in the z-axis direction from the center Vc of voxel V applied in non-linear interpolation according to the invention.

In the method according to the invention, the size of the reconstruction voxel V in the z-axis direction is given as Hv (see FIG. 6). Then, J points are arranged at equal intervals ΔZ vertically in the z-axis direction in a voxel V including a center point Vc, where ΔZ=Hv/J. Of these J points, MicroV(1), MicroV(2) ..., MicroV(J) defined as given above, consider first the uppermost one, MicroV(1). Back_MicroV(I,1) is obtained by back-projection of MicroV(1), by performing interpolation of projection data, for example linear interpolation, using data closest to the point where the extension of the straight line connecting the x-ray focal spot and MicroV(1) intersects the detector surface, for a given view I.

Next, back-projection as described above is performed with respect to all of the MicroV(J) to obtain respective Back_MicroV(I,J). In accordance with the following equation, the values Back_MicroV(I, J) obtained by back-projection with respect to all the MicroV(J) are added and averaged, and take the sum as the value Back(I) backprojected on to voxel V.

$$\text{Back}(I) = \sum_{j=1}^{J} \text{Back MicroV}(I,j)/J$$

By means of the above, complicated non-linear interpolation can-be performed with an inexpensive system layout and hardware construction capable only of linear interpolation. Also, with the method according to the invention, instead of backprojecting data on a straight line passing through the center of a voxel, the beam passing through the entire voxel is backprojected. The present invention is therefore a more accurate method and can take into account of spreading of the x-ray beam.

Figure 7:
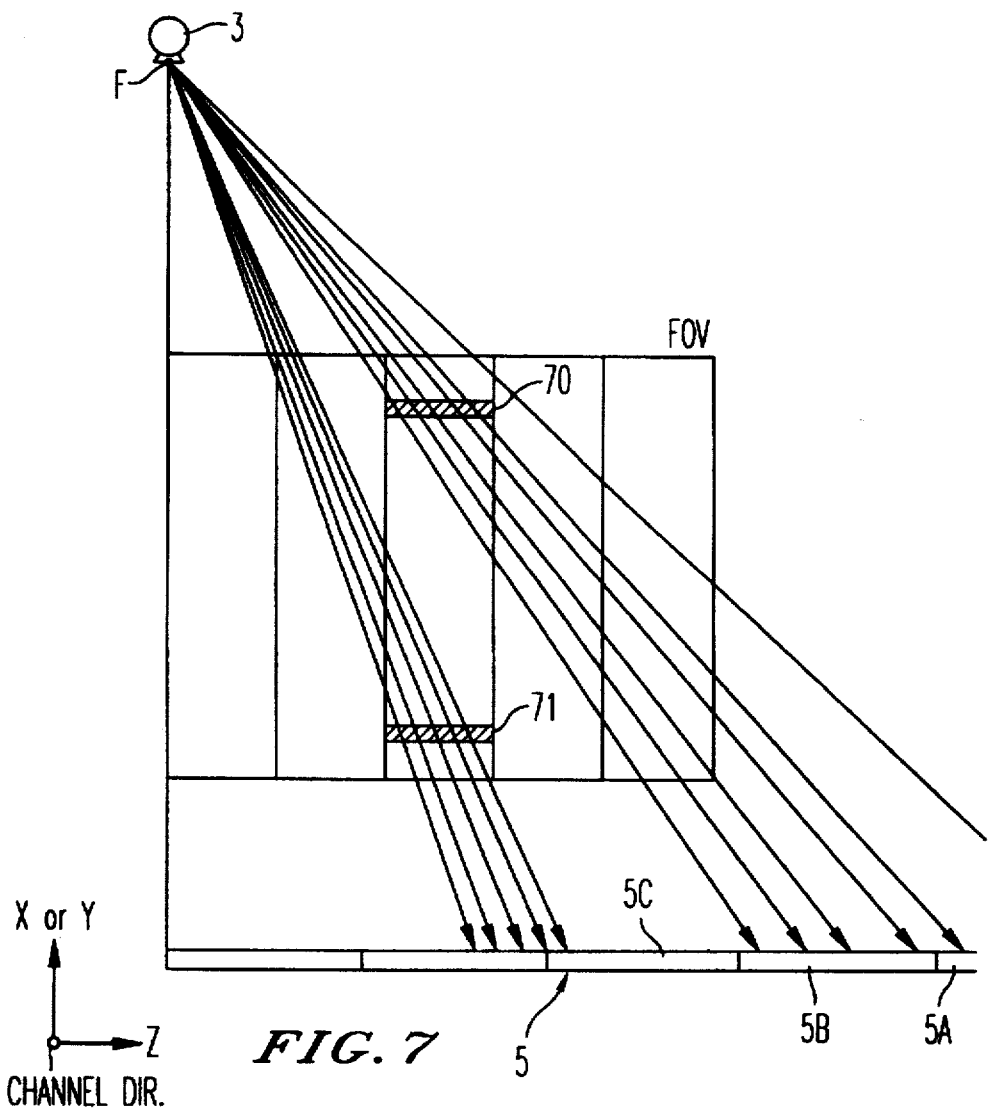
FIG. 7 is a diagram illustrating the relationship between voxel position and projection data employed in non-linear interpolation according to the invention.

As a result, as shown in FIG. 7, back-projection data for a voxel (voxels 70 and 71 are shown as examples) is compiled by suitably employing projection data of at least one row, dependent on the spread of the x-ray beam passing through the voxel, i.e. the position of the voxel or distance from the focal spot. Thus, the weighting (for a given detector) in respect of a given detector row is a function of the position of the point of intersection of the beam with the detector element and the position of the voxel:

W(detector row)=F(intersection position, voxel position)

Also, the weighting could be simplified by neglecting the position dependence. This does not produce noticeable deterioration of the image quality if it is arranged to make the weights equal to the weight of the above equation at the center of rotation:

W(detector row)=F(intersection position)

For example, in the case of back-projection for a given voxel, it will be assumed that the weights from the position of the point of intersection up to the first to Nth rows can be found as follows with the preceding equation:

W(1)=0.0, W(2)=0.0, W(3)=0.3, W(4)=0.6, W(5)=0.1, W(6)=W(7)=. . .=W(N)=0.0.

If the weight in the channel direction is taken as being WT_CH, the back-projected data are given by the following equation:

Back(I)=Σ[W(N)[WT_CH·D(n,N)+(1−WT_CH)·D(n+1,N)]]·WT_CH[W(3)·D(n,3)+W(4)·D(n,4)+W(5)·D(n,5)]+(1−WT_CH)[W(3)·D(n+1,3)+W(4)·D(n+1,4)+W(5)·D(n+1,5)]

Also, since, in the method described above, the weights of the backprojection at each point are practically the same, the data can be added up and averaged prior to backprojection. Specifically, in a modification of the first embodiment, consider the uppermost MicroV(1) of the J points defined as described above.

Pre_Back_MicroV(1,1) is obtained by performing interpolation, using data of the channels closest to the point where the straight line joining the focal spot and Microv(1), when extended, intersects the detector surface, in a given view I. The respective Pre_Back_MicroV(I,J) are then obtained by interpolation in the same manner as described above, for all the MicroV(J). The value obtained summing and averaging the Pre_Back-MicroV(I,j) for all the MicroV (j) is made Pre_Back(I). The value obtained by back-projecting on to voxel V of Pre_Back(I) is made Back(I).

The calculation time for back-projection can thereby be very greatly reduced and the error involved in performing backprojection just once instead of for all the MicroV(J) is practically negligible. This single backprojection of Pre_Back data is not limited to addition and averaging. For example, weighting and addition could also be used.

Although as described above, voxel V was subdivided at equal intervals, the intervals need not necessarily be equal. Also, although the number of subdivisions was taken as J=5, the number of subdivisions could be chosen at will. Also, there is no restriction on the type of interpolation employed. Although adding and averaging were employed above, alternatively, weighted addition or another method could be employed. More complicated non-linear interpolation can be performed by changing the sub-voxel interval and the number of sub-voxels and by performing weighted addition.

Also, it would be possible to perform non-linear interpolation using a function taking into account the spread of the beam produced by position dependence, as in FIG. 7, from the position of the voxel and the position of the point of intersection of the detector surface with the extension of the straight line connecting the focal spot and the center of the voxel.

A first example of the weighting dependent upon the intersection position and the voxel position will be described. Both the multi-slice cone beam reconstruction and the Foldkemp reconstruction (basic reconstruction methods), in static or helical scans, consist of the convolution stage and the backprojection stage. At the backprojection stage, the image is generated pixel by pixel, from contributions of all the views to each pixel. The contribution of each view to a specific pixel is determined by interpolation of data points belonging to individual detectors. In other words, the contribution of each view to a specific pixel is a weighted sum of data of some detectors. Thus, within the framework of all the currently known reconstruction methods for x-ray cone beam CT, the choice of the detector segment and the weights to be used in this interpolation process contain all the information about the dependence of the image on its axial coordinate.

When the finite reconstruction width method according to the invention is used, in each of these reconstruction methods, the point-wise reconstruction is replaced with a reconstruction along a segment of length M in the axial direction. This is done by summing (in the discrete process) or integrating (in the continuous process) of the weights corresponding to each point of the segment where the weights are calculated according to the regular rules, for point-wise images, of the specific basic reconstruction method being used. The differences and variations between the basic reconstruction methods, in static or helical scans, can all be presented in terms of geometrical differences which are described below.

Figure 8:
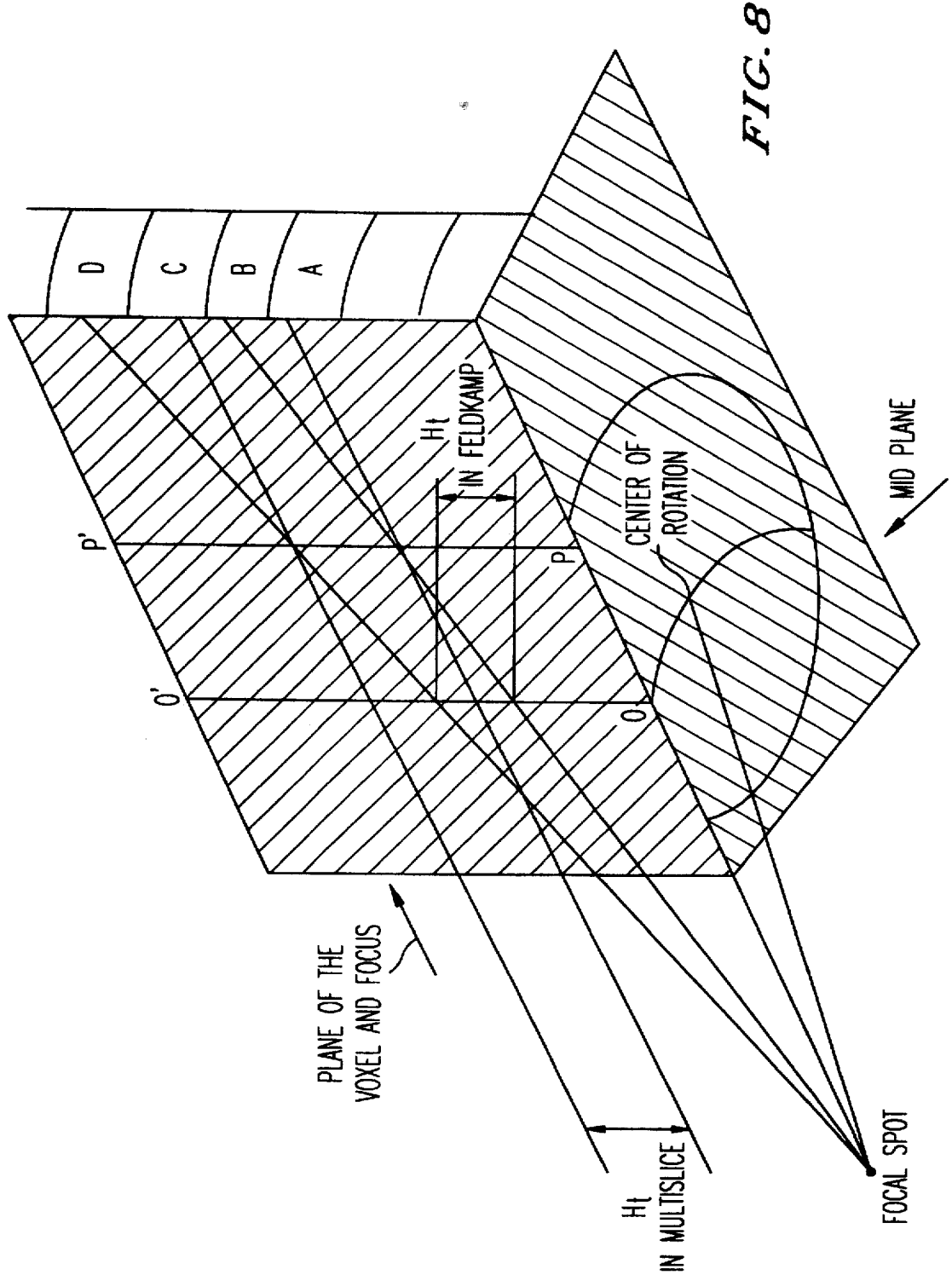
FIG. 8 is a diagram illustrating the geometry of cone-beam reconstruction.
Figure 9:
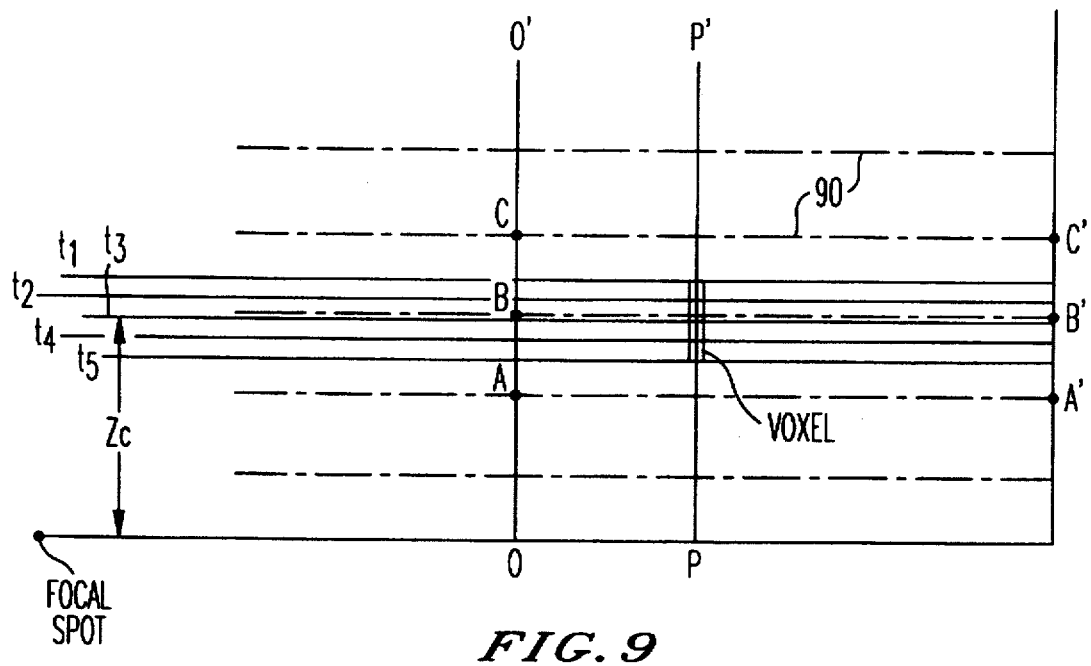
FIG. 9 is a diagram of the geometry associated multi-slice backprojection reconstruction.
Figure 10:
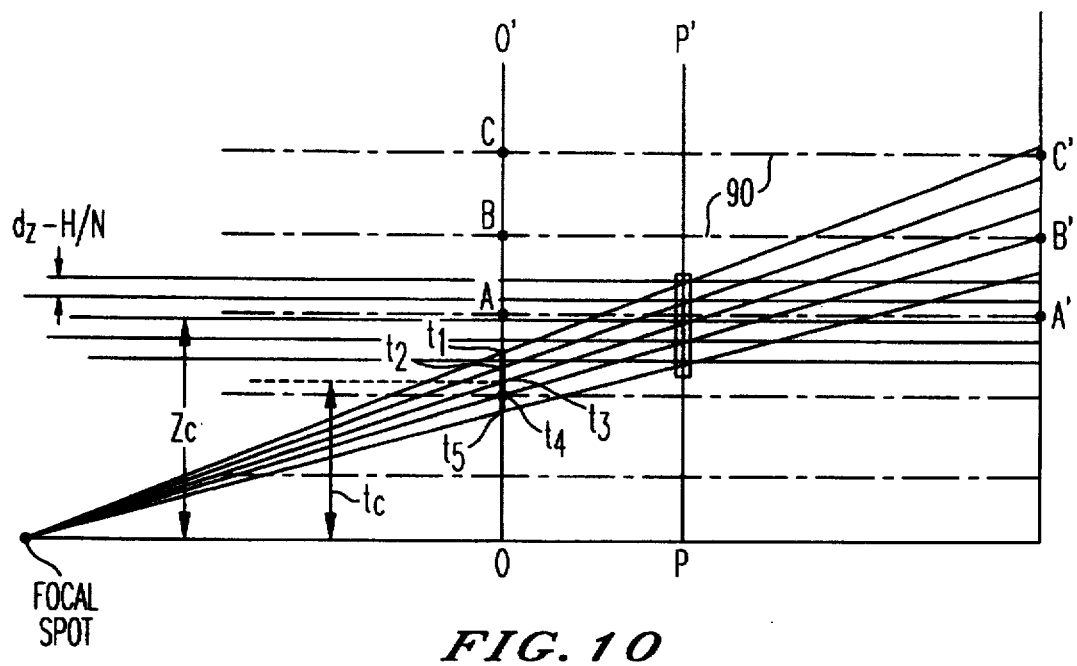
FIG. 10 is a diagram of the geometry associated Foldkemp multi-slice backprojection reconstruction.

FIG. 8 shows the basic geometry of x-ray cone beam reconstruction, related to the backprojection contribution of one view to an arbitrary voxel. An x-ray beam is irradiated from the focal spot through the subject onto detector segments A–D. FIGS. 9 and 10 show the plane defined as containing the line from the focal spot to the voxel in question and being perpendicular to the mid-plane. Point O is the intersection of this plane with the arc lying in the mid-plane, centered at the focal spot and passing through the center of rotation. Point P is the perpendicular projection of the center of the voxel into mid-plane. The lines P—P', and O—O' are perpendicular to the mid-plane.

FIG. 9 shows the geometry governing the backprojection contribution in the case of multi-slice reconstruction method for a voxel having contributions from detectors A–C, while, FIG. 10 shows this geometry for the Feldkamp multi-slice reconstruction for a voxel having contributions from detectors A–C. In the case of the Foldkemp reconstruction all the quantities defined on the axial direction such as z, the height of the reconstruction slice center and H, the width of the reconstruction slice, and the detector segment axial pitch D, are projected on the line O–O':

$$t_c = z_c \times \frac{FCD}{FVDP} \quad H_t = H \times \frac{FCD}{FDVP} \quad D_t = D \times \frac{FCD}{FDD}$$

where FCD is the focal spot to center of rotation distance, FDVP is the focal spot to voxel distance projected onto the mid-plane and FDD is the focal spot to detector distance. For the multi-slice reconstruction, the quantities H, D and $z_c$ do not change when projected, but are referred to as $H_c$, $D_c$ and $z_c$ for a uniform description of the weighting below.

Here, the weighting for a voxel (such as 61 in FIG. 6, or as shown in FIG. 12(a)) where only two detector elements, one in each of two adjacent rows, contribute to the sub-voxels is explained. The individual sub-voxel weights are calculated separately and weighted. For the case of linear interpolation of voxels in two rows, the weights are, for elements A and B with center positions $t_A$ and $t_B$:

$$W_{Ai} = \frac{(t_B - t_i)}{D_t} \text{ and } W_A = \frac{(\Sigma W_{Ai})}{N}$$

$$W_{Bi} = \frac{(t_A - t_i)}{D_t} \text{ and } W_B = \frac{(\Sigma W_{Bi})}{N}$$

where $t_i$ is the position of the extended beam through the sub-voxel on detectors A and B, N is the number of sub-voxels, and $D_t$ is the spacing between centers of adjacent detector elements (the axial length of a detector element).

A second example is the case where the sub-voxels have contributions from three detectors A, B and C in adjacent rows with center positions 90 given as $t_A$, $t_B$ and $t_C$. In FIG. 7 the voxel 70 is in this category where the top three sub-voxels (1, 2 and 3) have contributions from the two detector elements 5A and 5B (A and B) while the lower two sub-voxels (4, 5) have contributions from the detector elements 5B and 5C (B and C). FIG. 12(b) is also an example of this situation. The weights are determined as follows:

$$W_{Ai} = \frac{(t_B - t_i)}{D_t} \quad i = 1,2,3 \text{ and } W_A = \frac{(W_{A1} + W_{A2} + W_{A3})}{5}$$

$$W_{Bi} = \frac{(t_i - t_A)}{D_t} \quad i = 1,2,3; \quad W_{Bi} = \frac{(t_C - t_i)}{D_t} \quad i = 4,5; \quad W_B = \frac{(\Sigma W_{Bi})}{5}$$

$$W_{Ci} = \frac{(t_i - t_B)}{D_t} \quad i = 4,5 \text{ and } W_C = \frac{(W_{C4} + W_{C5})}{5}$$

$$W_{Bi} = 1 - W_{Ai} \quad i = 1,2,3 \text{ and } W_{Bi} = 1 - W_{Ci} \quad i = 4,5$$

In the above examples linear weighting is used but other types of weighting, such as nonlinear weighting and weighted averaging given as the following respective equations could be used:

$$W_{Ai} = \frac{(t_B - t_i)^2}{\Delta Z} \text{ and } W_A = (w_1 \cdot W_{A1} + \ldots + w_N \cdot W_{AN})$$

where $w_N$ are coefficients used in the weighted averaging. Also, while an odd number of sub-voxels are shown in FIG. 6, an even number could be used.

In a third example the number of sub-voxels N→∞, a continuous process. Summation is replaced by integration and the averaging (division by N) is replaced with division by $H_r$. This process in space-variant, i.e., voxel position dependent. The weights are calculated using a space-variant function.

Figure 14:
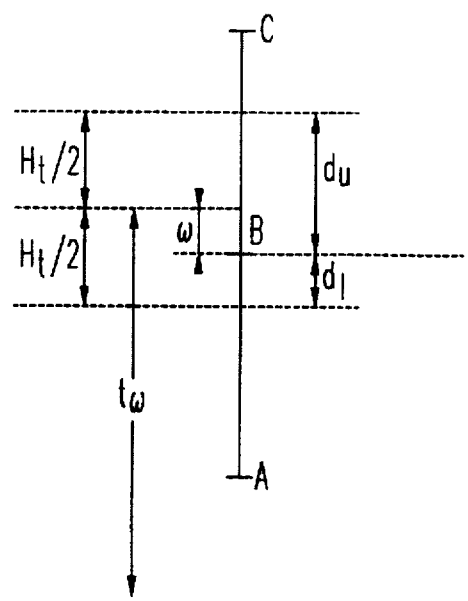
FIG. 14 is a diagram illustrating a relationship between a voxel and detector elements used in a continuous reconstruction process.

When only two detector elements contribute to the reconstruction process, the weights for the sub-voxels determined are the same as those in reconstruction calculated for the center of the entire voxel. The situation where three detectors contribute will therefore be discussed. Referring to FIG. 11, centers 90 of seven detector elements A–G (of size $D_t$) are shown with the extent of the reconstruction slice segment $H_r$ and the detector pitch $D_t$ shown. The weights are calculated as follows:

$$W_A = \frac{1}{H_t} \int_0^{d_t} \frac{t}{D_t} \, dt - \frac{d_t^2}{2H_t D_t} \text{ and }$$

$$W_C = \frac{1}{H_t} \int_0^{d_u} \frac{t}{D_t} \, dt - \frac{d_u^2}{2H_t D_t}$$

where $d_u$ and $d_l$ are the distances of the upper and lower edge of the reconstruction voxel segment from the center of the center detector of the three contributing to the reconstruction. For example, the central detector B and the distances $d_u$ and $d_l$ are shown in FIG. 14. The weight for segment B is given as $$W_B = 1 - W_A - W_C$$

which is easily verified by independent integration.

Figure 13:
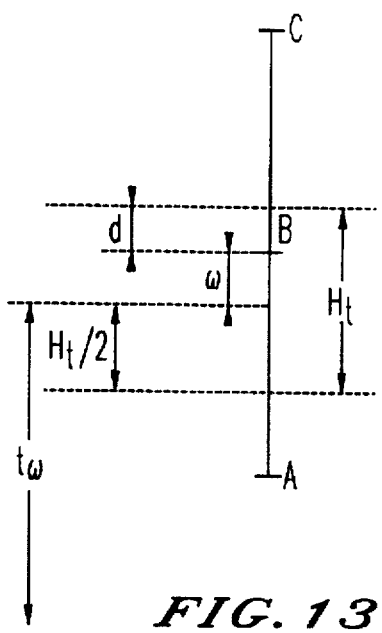
FIG. 13 is a diagram illustrating a relationship between a voxel and detector elements used in a continuous reconstruction process.

Instead of using the two distances $d_u$ and $d_l$, only one parameter w, the signed distance of the closest detector element to the center of the reconstruction voxel. The distance $d_w$ between the center of the closest detector and the upper edge of the reconstruction voxel is determined as $t_B - t_W$ and $t_W - t_B$, as shown in FIGS. 13 and 14, respectively. The distance w is positive if the center of the reconstruction voxel is below the detector center and negative if above (see FIG. 12). The weights are now determined as $$W_A = \frac{\left(\frac{H_t}{2} - w\right)^2}{2H_t D_t} \text{ and } W_C = \frac{\left(\frac{H_t}{2} + w\right)^2}{2H_t D_t}$$

where WB=1−WA−WC as in the above example.

Figure 15:
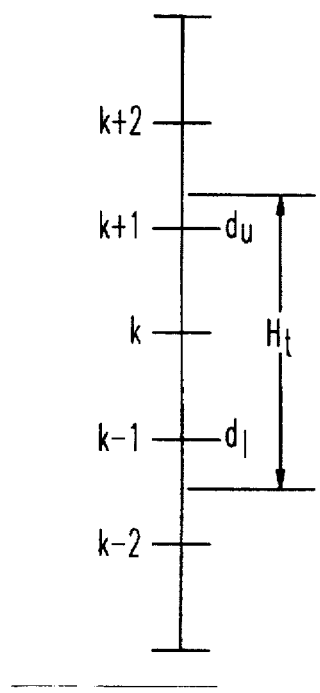
FIG. 15 is a diagram illustrating a relationship between a voxel and detector elements used in a continuous reconstruction process for an arbitrary number of detector elements.
Figure 16:
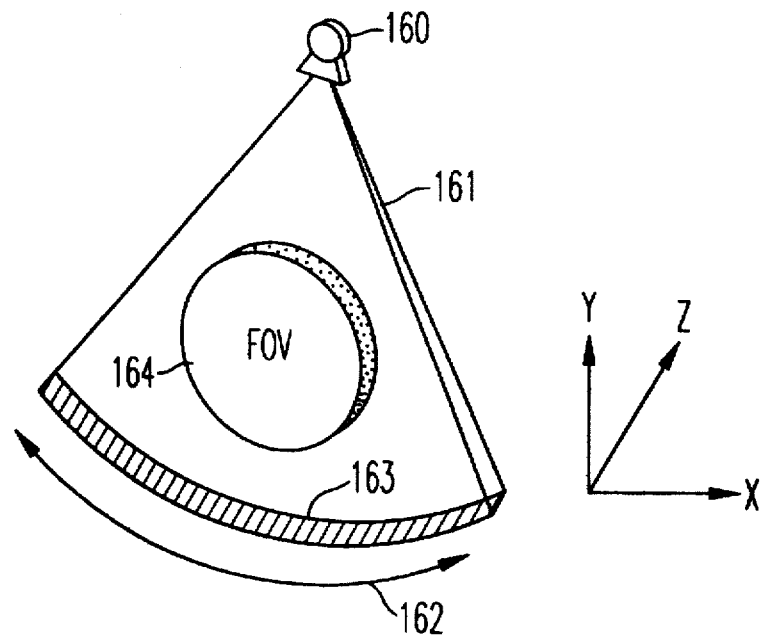
FIG. 16 is a perspective view of a one-dimensional array type x-ray detector.
Figure 19:
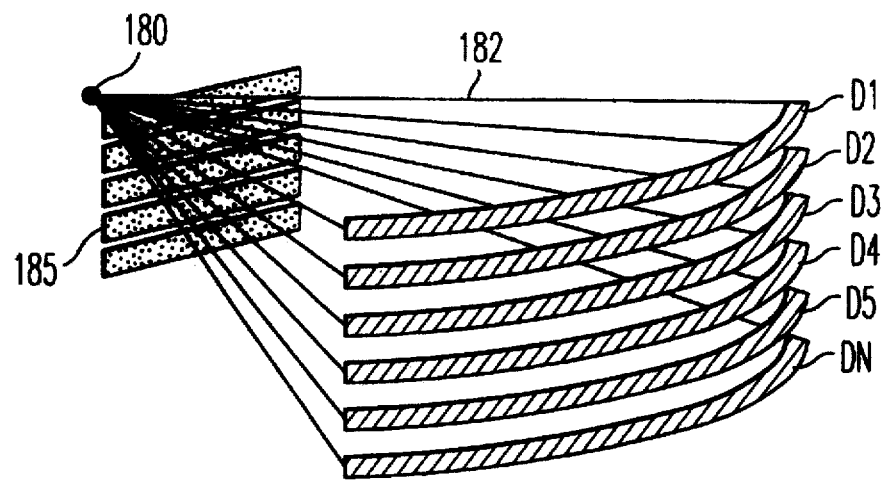
FIG. 19 is a diagram illustrating cone-beam scanning.

For the general case, when an arbitrary number of detector elements contribute to the reconstruction, the weight are determined as follows. First the following parameters are calculated:

$$l_u = \text{int}\left(\frac{0.5H_t + u}{D_t}\right); \; d_u = 0.5H_t - l_u \times D_t + u$$

Where the function int(x) defines the integer value of the number $$l_l = \text{int}\left(\frac{0.5H_t - u}{D_t}\right); \; d_l = 0.5H_t - l_l \times D_t - u$$

x (the largest integer smaller than x). In the notation appropriate for this case the detector element closest to the center of the reconstruction slice segment, $t_C$, is denoted as detector element k, $l_u+1$ is the number of contributing detector elements above detector segment k, and $l_l$ is the number of contributing detector segments below segment k. The total number of contributing element is thus $l_u+l_l+3$. For the assignment of the weights in the general case, it is convenient to sort the contributing detector elements according to their position with respect to the borders of the reconstruction voxel segment. This will be done by considering an example of 5 contributing detectors as illustrated in FIG. 15.

Detector element k+2 is an upper edge detector element, detector element k+1 is below the upper edge detector element, detector segment k−2 is a lower edge detector element, and detector element k−1 is above a lower edge detector element. Finally, a detector element relation to the reconstruction sub-voxel is none of the above relations is an inside detector element, as is detector element k in this example. The calculation of the weights is now done according to the detector element, starting with the upper and lower edge detector segments:

$$W_{k+2} = \frac{d_u^2}{2} H_t D_t$$

$$W_{k-2} = \frac{d_l^2}{2} H_t D_t$$

while for the detector elements adjacent to the upper and lower edge detector elements:

$$W_{k+1} = \frac{D_t}{2H_t} + \frac{d_u}{2H_t} - \frac{d_u^2}{2H_tD_t}$$

$$W_{k-1} = \frac{D_t}{2H_t} + \frac{d_l}{2H_t} - \frac{d_l^2}{2H_tD_t}$$

and for inside detector elements:

$$W_k = \frac{D_t}{H_t}$$

In the above determinations it was assumed that the weights multiplying the contributions from the detector elements are obtained by linear interpolation. However, the invention is not so limited. The determinations described above can be applied to any other interpolation methods, for example, higher order interpolation methods. It should also be noted that other space-variant functions may be used, only one example is given to explain the invention. Non-linear weighting may also be used, as well as weighted averaging.

The invention was described using the center of the detector elements. Another location in the detector element may be chosen.

There are innumerable weighting coefficient curves for non-linear interpolation, including the Gaussian function, trigonometrical function, and higher-order functions. A comparatively straightforward method has been described here to illustrate the invention, but the invention is not so limited.

What is claimed is:

1. A computed tomography system, comprising:
   an x-ray source;
   a detector array having a plurality of detector elements;
   a projection data circuit connected to said detector array;
   a sub-voxel circuit connected to said projection data circuit; and
   a backprojection circuit connected to said projection data circuit.

2. A system as recited in claim 1, comprising:
   a weighting circuit connected to at least one of said sub-voxel circuit and said backprojection circuit.

3. A system as recited in claim 1, comprising:
   an interpolation circuit connected to said projection data circuit.

4. A system as recited in claim 1, wherein said sub-voxel circuit comprises:
   means for determining a plurality of points within a voxel of a subject being irradiated by an x-ray beam;
   means for determining respective x-ray paths from said x-ray source through said plurality of points to said detector array.

5. A system as recited in claim 4, wherein said backprojection circuit performs backprojection for each of said plurality of points and produces a respective plurality of backprojection data, said system comprising:
   means for weighting said plurality of backprojection data; and
   means for determining backprojection data for said voxel based upon said weighted plurality of backprojection data.

6. A system as recited in claim 2, wherein said weighting circuit comprises:
   means for weighting projection data based upon a position of an intersection of an x-ray beam, through a sub-voxel, on one of said plurality of detector elements.

7. A system as recited in claim 6, wherein said means for weighting weights based also upon a position of said sub-voxel.

8. A system as recited in claim 2, wherein said weighting circuit comprises means for weighting and adding projection data prior to said backprojection circuit performing backprojection.

9. A system as recited in claim 2, wherein said weighting circuit comprises:
   means for weighting projection data corresponding to a voxel having a contribution from only two of said detector elements as:

$$W_{Ai} = \frac{(t_B - t_i)}{D_t} \text{ and } W_A = \frac{(\Sigma W_{Ai})}{N}$$

$$W_{Bi} = \frac{(t_A - t_i)}{D_t} \text{ and } W_B = \frac{(\Sigma W_{Bi})}{N}$$

where $W_A$ and $W_B$ are weights associated with detector elements A and B, $t_A$ and $t_B$ are predetermined positions in said detector elements A and B, respectively, N is a number of sub-voxels within said voxel, $D_t$ is a spacing between said predetermined positions, and $t_i$ is a position of the an x-ray beam through a sub-voxel on detectors A and B.

10. A system as recited in claim 2, wherein said weighting circuit comprises:
   means for weighting projection data corresponding to a voxel having a contribution from only three adjacent ones of said detector elements as:

$$W_{Ai} = \frac{(t_B - t_i)}{D_t} \text{ and } W_A = \frac{(\Sigma W_{Ai})}{N}$$

for beams I incident between predetermined positions of detector elements A and B, where $t_B$ is said predetermined positions in said detector element B, N is a number of sub-voxels within said voxel, $D_t$ is a spacing between said predetermined positions, and $t_i$ is a position of the an x-ray beam through a sub-voxel on detector elements A and B;

for beams I incident between a predetermined position in detector element C and said predetermined position in detector element B; and as $$W_{Ci} = \frac{(t_i - t_B)}{D_t} \text{ and } W_C = \frac{(\Sigma W_{Ci})}{N}$$

$$W_{Bi} = \frac{(t_i - t_A)}{D_t} \quad W_{Bi} = \frac{(t_C - t_i)}{D_t} \quad W_B = \frac{(\Sigma W_{Bi})}{N}$$

for beams I incident on between said predetermined positions in detector elements A,B and B,C, respectively.

11. A system as recited in claim 1, comprising:
   means for determining an x-ray path for a plurality of paths at a plurality of points in a voxel; and
   means for interpolating projection data for each of said plurality of points;
   wherein said backprojection circuit back-projects interpolation data and produces back-projection data for each of said plurality of points.

12. A computed tomography system, comprising:
   an x-ray source;
   a detector array having a plurality of detection elements and disposed to receive x-rays emitted from said x-ray source; and
   a projection data circuit connected to said detector array;

a space-variant weighting circuit connect to said projection data circuit; and a sub-voxel backprojection circuit connected to said projection data circuit.

13. A system as recited in claim 12, wherein said sub-voxel backprojection circuit comprises:

means for determining a plurality of points within a voxel of a subject being irradiated by an x-ray beam;

means for determining respective x-ray paths from said x-ray source through said plurality of points to said detector array.

14. A method of operating a computed tomography system, comprising:

obtaining projection data; and backprojecting said projection data using a plurality sub-voxels.

15. A method as described in claim 14, wherein said system includes an x-ray source, said method comprising:

dividing a voxel of a subject irradiated by said x-ray source into a plurality of sub-voxels; and obtaining sub-voxel projection data for the sub-voxels; and backprojecting using said sub-voxel projection data.

16. A method of operating a computed tomographic system, comprising:

dividing a voxel of a subject in to a plurality of sub-voxels; and obtaining backprojection data for said plurality of sub-voxels.

17. A method as recited in claim 16, wherein said method includes an x-ray source and an x-ray detector, and dividing said voxel comprises:

determining a plurality of points within said voxel about a center point of said voxel corresponding to said plurality of sub-voxels;

determining a plurality of x-ray paths from said x-ray source through said plurality points to said detector, respectively; and backprojecting each of said sub-voxels.

18. A method as recited in claim 17, wherein backprojecting said sub-voxels comprises:

obtaining projection data;

interpolating sub-voxel projection data for said sub-voxels from said projection data; and backprojecting said sub-voxel projection data.

19. A method as recited in claim 18, wherein interpolating said sub-voxel projection data comprises:

interpolating said sub-voxel data from 2N rows of said projection data, where N is an integer greater than 1.

20. A method as recited in claim 16, wherein obtaining backprojection data comprises:

obtaining sub-voxel backprojection data for each of said sub-voxels; and weighting said sub-voxel backprojection data.

* * * * *